United States Patent [19]

Sun et al.

[11] Patent Number: 5,755,739
[45] Date of Patent: May 26, 1998

[54] ADAPTIVE AND MORPHOLOGICAL SYSTEM FOR DISCRIMINATING P-WAVES AND R-WAVES INSIDE THE HUMAN BODY

[75] Inventors: Weimin Sun, Plymouth, Minn.; Pamela A. Abshire, Baltimore, Md.; Eric J. Panken, Minneapolis; William J. Combs, Eden Prairie, both of Minn.

[73] Assignee: Medtronic, Inc., Minneapolis, Minn.

[21] Appl. No.: 759,902

[22] Filed: Dec. 4, 1996

[51] Int. Cl.⁶ .......................... A61N 1/362; A61B 5/0464
[52] U.S. Cl. .......................... 607/14; 600/517; 600/518
[58] Field of Search .......................... 607/9, 14; 600/509, 600/510, 514–518, 521

[56] References Cited

U.S. PATENT DOCUMENTS

| | | |
|---|---|---|
| 3,903,897 | 9/1975 | Woollons et al. . |
| 4,365,639 | 12/1982 | Goldreyer . |
| 4,721,114 | 1/1988 | DeFault et al. . |
| 4,751,931 | 6/1988 | Briller et al. . |
| 4,793,361 | 12/1988 | DeFault . |
| 4,799,486 | 1/1989 | DeFault . |
| 4,825,870 | 5/1989 | Mann et al. . |
| 5,000,189 | 3/1991 | Throne et al. . |
| 5,092,343 | 3/1992 | Spitzer et al. . |
| 5,280,792 | 1/1994 | Leong et al. . |
| 5,292,348 | 3/1994 | Saumarez et al. . |
| 5,379,776 | 1/1995 | Murphy et al. . |
| 5,400,795 | 3/1995 | Murphy et al. . |
| 5,404,880 | 4/1995 | Throne . |

OTHER PUBLICATIONS

"Dual Channel P–Wave Detection in the Surface ECG, Via the LMS Alogrithm.", DuFault et al., pp. 325–328.

"Adaptive Noise Cancelling: Principles and Applications," Bernard Widrow, et al., Mar. 24, 1975, Aug. 7, 1975, pp. 1692–1716.

"An Alogorithm for Automatic P–Wave Detection in Single or Multiple Lead Surface ECGs," R. DuFault et al., pp. 117–119.

"Cancelling the Cardiogenic Artifact in Impedance Pneumography," Sahakian et al., pp. 855–859 .

"P–Wave Detection by an Adaptive QRS–T Cancellation Technique," Yi–Sheng et al., pp. 249–252.

"Identification of Ventricular Tachycardia with use of the Morphology of the Endocardial Electrogram," Langberg et al., Jun. 1988, pp. 1363–1369.

(List continued on next page.)

*Primary Examiner*—Jeffrey R., Jastrzab
*Attorney, Agent, or Firm*—Thomas F. Woods; Harold R. Patton

[57] ABSTRACT

The present invention is a method and apparatus for processing a sensed atrial electrogram in conjunction with a sensed ventricular electrogram. The present invention permits accurate discrimination of atrial P-waves from far field ventricular events such as far field R-waves and avoids oversensing such far field ventricular events as atrial sense events and undersensing atrial events occurring within a fusion beat masked by a far field ventricular event in the atrial electrogram. Atrial channel trigger signals are generated in response to sensed P-waves and far field R-waves in the atrial electrogram, and ventricular trigger signals are generated in response to sensed R-waves in the ventricular electrogram. In response to each ventricular channel trigger signal, the sensed atrial electrogram signal is adaptively filtered for an adaptive filter time window only to remove the far field R-wave signal from the sensed atrial electrogram signal while avoiding adaptive filtering of the sensed atrial electrogram signal at other times. In response to each atrial channel trigger signal, the adaptively filtered, sensed atrial electrogram signal is subjected to morphological analysis in respect of a morphological model of a P-wave only during a morphology time window. In this manner, P-waves in the sensed atrial electrogram signal are detected and far field R-waves in the sensed atrial electrogram signal are not mistakenly detected as P-waves, while morphological analysis of the sensed atrial electrogram at other times is avoided.

28 Claims, 5 Drawing Sheets

OTHER PUBLICATIONS

"A Comparison of Four New Time–Domain Techniques for Discriminating Monomorphic Ventricular Tachycardia from Sinus Rhythm Using Ventricular Waveform Morphology.", Throne et al., Jun. 1991, pp. 561–570.

"Detection of Atrial Activation By Tranventricular Electrogram Morphology Analysis," Greenhut et al., Jun. 1993, pp. 1293–1303.

"Far Field R–Wave Sensing—An Old Problem Repeating." Schuller et al. Apr. 1996. p. 631→Pace. Naspe Abstracts (264).

ADAPTIVE AND MORPHOLOGICAL SYSTEM FOR DISCRIMINATING P-WAVES AND R-WAVES INSIDE THE HUMAN BODY

CROSS-REFERENCE TO RELATED APPLICATION

Reference is hereby made to commonly assigned, co-pending U.S. patent application Ser. No. filed Dec. 4, 1996 entitled "WAVELET HIDDEN MARKOV MODELING METHOD FOR CARDIAC EVENT WAVE DETECTION AND ARRHYTHMIA ANALYSIS," naming Weimin Sun et al. as inventors, and having Attorney Docket No. P-3594, the disclosure of which is hereby incorporated by reference herein in its entirety.

FIELD OF THE INVENTION

The present invention relates to implantable cardiac stimulators and monitors and particularly to the detection and discrimination of P-waves originating from depolarization of the atrium from R-waves originating from depolarization of the ventricles in atrial electrogram (A-EGM) signals picked up by implanted atrial electrodes.

BACKGROUND OF THE INVENTION

Dual chamber, implantable cardiac stimulators, e.g., pacemakers and pacemaker-cardioverter-defibrillators (PCDs) or other implantable cardioverter-defibrillators (ICDs), and cardiac monitors are widely known that are designed to sense and validly distinguish P-waves from R-waves for storage of data or to time other operations, e.g. atrial and/or ventricular pacing in synchrony with the sensed underlying heart rhythm, or to discriminate atrial and ventricular tachyarrhythmias.

Figure 1:
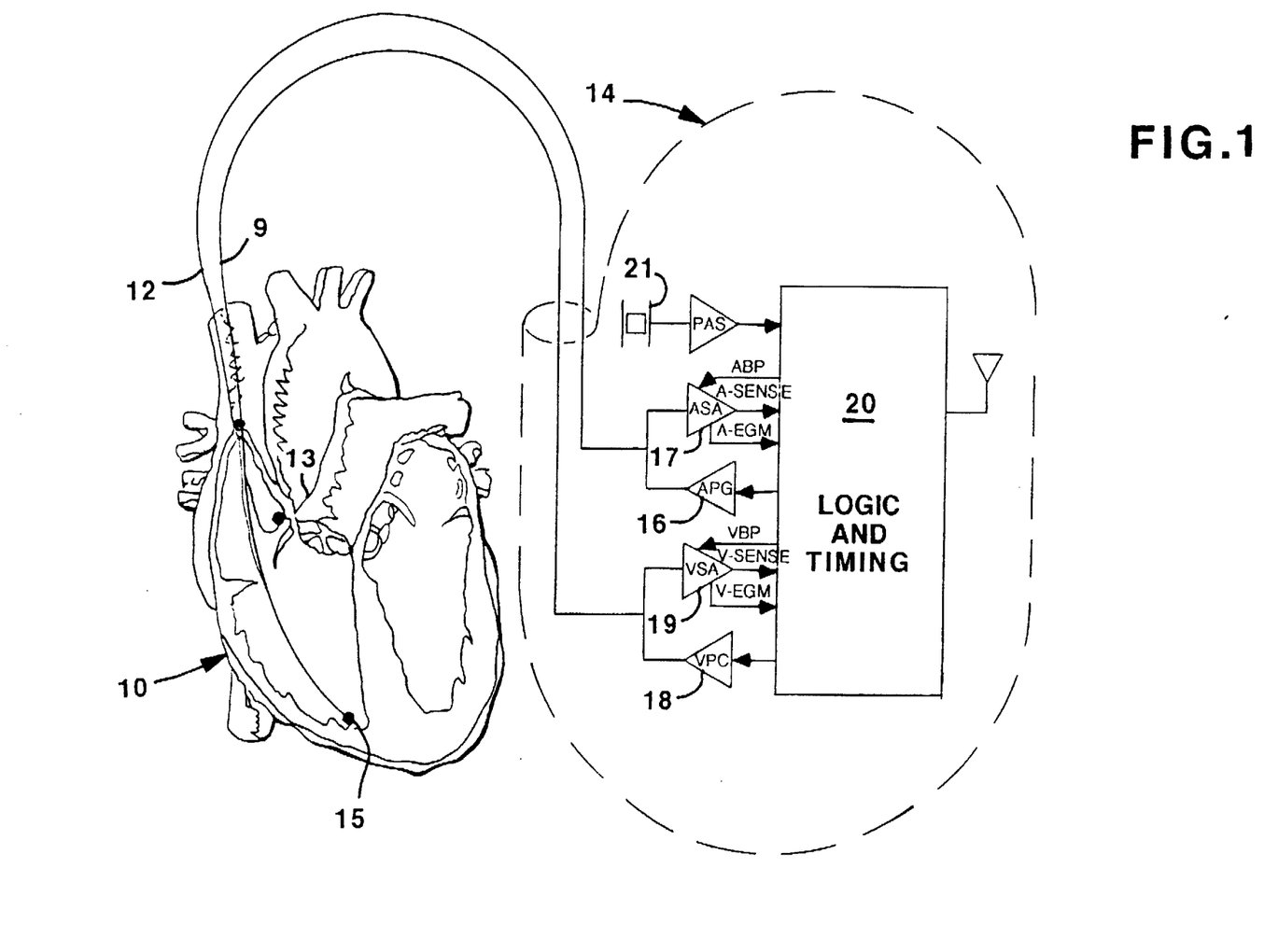
FIG. 1 is a simplified, conventional, dual chamber pacemaker system including atrial and ventricular leads and a dual chamber IPG in which the present invention may be implemented.

FIG. 1 schematically depicts components of a typical dual chamber stimulator or monitor and specifically components of a multi-mode DDD pacemaker system comprising an implantable pulse generator (IPG) 14 coupled with atrial and ventricular leads 12 and 9 extending into the right atrium and ventricle, respectively, of the heart. The IPG 14 is provided with atrial and ventricular sense amplifiers 17 and 19, respectively, coupled through leads 12 and 9, respectively, to atrial electrode(s) 13 implanted in the atrium and ventricular electrode(s) 15 implanted in the ventricles, respectively, that are intended to sense P-waves and R-waves originating in the right atrium and ventricle, respectively.

Typically, the atrial sense (A-SENSE) event is determined from the A-EGM from a unipolar or bipolar, atrial lead 12 having one or two pace/sense electrodes 13 in contact with the atrium, and the ventricular sense (V-SENSE) event is determined from the V-EGM from a unipolar or bipolar ventricular lead 9 having one or two pace/sense electrodes 15 in contact with the ventricle. The atrial and ventricular sense amplifiers 17 and 19 employ sense criteria for distinguishing valid P-waves and R-waves, respectively, from electrical noise and artifacts. The incoming A-EGM and V-EGM signals are filtered to attenuate commonly encountered electrical noise and muscle artifacts and the amplitudes of the signals are compared against atrial and ventricular sense thresholds Because the amplitude of the P-wave is significantly lower than that of the QRS complex and particularly of the R-wave, the atrial sense threshold may be set lower than the ventricular sense threshold. Consequently, the QRS complex and the ventricular pace (V-PACE) pulse artifact often appear in the A-EGM conducted by the atrial lead 12 to the atrial sense amplifier 17 and often have an amplitude exceeding the P-wave sense threshold. In this context, the sensed QRS complex or R-wave is referred to as the "far field R-wave" and the sensing of the far field R-wave or V-PACE artifact is referred to as "oversensing". Such oversensing is even more of a problem when a unipolar atrial electrode 13 is used since the major portion of the QRS gradient falls between the atrial tip electrode 13 and the indifferent plate consisting of the can of the IPG 14.

Oversensing of the far field R-wave from the A-EGM on the atrial pacing lead has long been an issue of concern in implantable dual chamber pacing systems as discussed for example, in the background of U.S. Pat. No. 3,903,897. As also disclosed in U.S. Pat. No. 4,825,870, time windows may also be set to detect the near coincidence of the A-SENSE and V-SENSE events and disregard the A-SENSE event. But these approaches may lead to undersensing of legitimate P-waves occurring in a fusion beat with a QRS complex.

One approach to minimizing the amplitude of the far field R-wave in the A-EGM is to minimize the far field QRS spatial gradient propagated to the atrium through the use of closely spaced atrial electrode pairs carefully oriented in the atrium as shown for example, in U.S. Pat. No. 4,365,639. Both approaches of the '897 and '639 patents are also directed to optimizing the A-EGM sensing performance of the so-called "single pass A-V lead", where the bipolar or multi-polar atrial sense electrodes are positioned proximally on a single A-V lead body and effectively float in atrial blood in the right atrial chamber. In a further approach, it has long been desired to detect the far field P-wave from a ventricular electrode through suitable filtering and timing as described in the Greenhut, S. E. et al. article "Detection of Atrial Activation by Intraventricular Electrogram Morphology Analysis: A Study to Determine the Feasibility of P Wave Synchronous Pacing from A Standard Ventricular Lead", PACE 1993; 16:1293–1303.

As a practical matter, use of the single pass A-V lead electrode(s) or the ventricular electrode does not admit of adequate P-wave sensing using conventional band pass filtering and threshold detection discrimination and detection techniques, nor, in the pacing context, do they allow for atrial pacing. Consequently, to date, separate atrial and ventricular leads and electrodes are employed in implantable systems of the type listed at the outset. However, with the typically employed lead and electrode system depicted in FIG. 1, where the atrial sense electrode(s) is in firm attachment in the atrial appendage, oversensing of far field R-waves and V-PACE artifacts as A-SENSE events can occur. To prevent triggering of sense events in response to a pace pulse, the logic and timing circuit 20 sets and times out atrial and ventricular blanking periods (ABP and VBP) when either an A-PACE or a V-PACE pulse is triggered, respectively. The atrial and ventricular sense amplifiers 17 and 19 are effectively disconnected from the atrial lead 12 and ventricular lead 9 during the ABP and VBP to protect the respective sense amplifier circuit from high signal levels. In addition, an atrial refractory period (ARP) is commenced in response to the detection of an A-SENSE event and a further post-ventricular atrial refractory period (PVARP) is commenced upon detection of a V-SENSE. Similarly, the logic and timing circuit 20 sets and times out a ventricular sense amplifier refractory period (VRP) in response to the detection of at least a V-SENSE event and the triggering of an A-PACE or V-PACE pulse. Any A-EGM signal passing through the atrial sense amplifier 17 during the longer ARP or PVARP is considered to be noise and not used to reset the V-A escape interval and start the A-V delay interval. Instead, it may be interpreted as a noise artifact and used to actually prolong the refractory period. Similarly, any V-EGM signal passing through the ventricular sense amplifier 19 during the longer VRP is considered to be noise and not used to reset the A-V delay interval and start the V-A escape interval.

Figure 2:
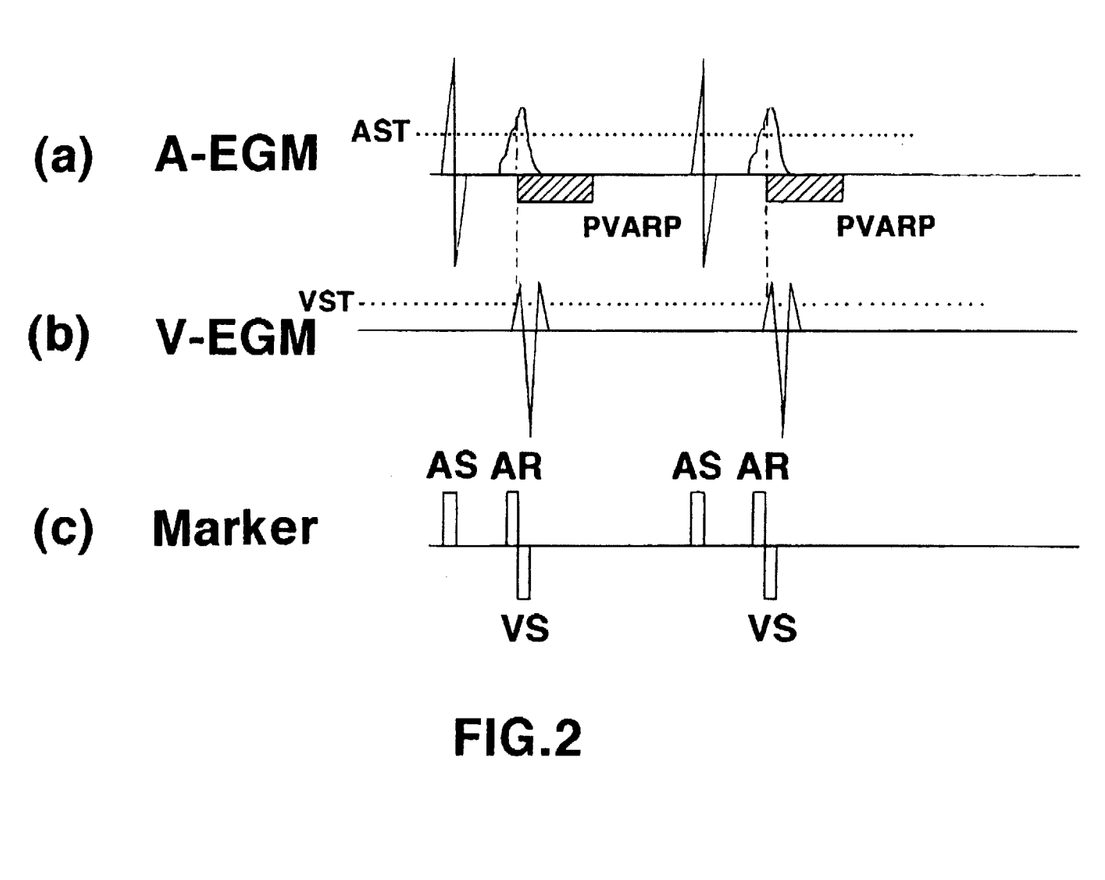
FIG. 2 illustrates an example of far field R-wave oversensing in the A-EGM that can occur.

FIG. 2 depicts a typical example of far-field R-wave oversensing that can occur particularly when an ectopic ventricular depolarization occurs prematurely in the heart cycle. Typically, the ectopic ventricular R-wave is sensed first at the ventricular electrode(s) 15, the ventricular sense amplifier 19 responds by generating the V-SENSE event. The logic and timing circuit 20 then generates the ABP in time to block detection of the far-field R-wave and an A-SENSE event. But to make sure that the V-SENSE event occurs first, it may be necessary to increase the A-SENSE threshold to a level that hinders the ability to sense the sometimes lower amplitude P-wave.

The A-EGM and V-EGM are depicted in tracings (a) and (b) in relation to A-SENSE and V-SENSE event markers in tracing (c) of FIG. 2. In tracing (a), the A-SENSE threshold AST is set low enough to detect the P-wave early in its rise time as indicated by marker AS, and the far field R-wave is also sensed as indicated by marker AR. In tracing (b), when the near field R-wave amplitude exceeds the V-SENSE threshold VST, the corresponding marker VS is generated in tracing (c). The V-SENSE event triggers the ABP and PVARP in tracing (a), but it is too late to stop generation of the A-SENSE event. The result may be that pacing in either chamber is inhibited, and the recurring ectopic beats may govern the heart rate, when it would be desirable to overdrive the intrinsic rate. Other device specific operations may be commenced or inhibited due to the apparent high atrial rate and/or the apparent abnormally short A-V delay presented to the logic and timing circuit 20 by the closely spaced A-SENSE and V-SENSE events.

Figure 3:
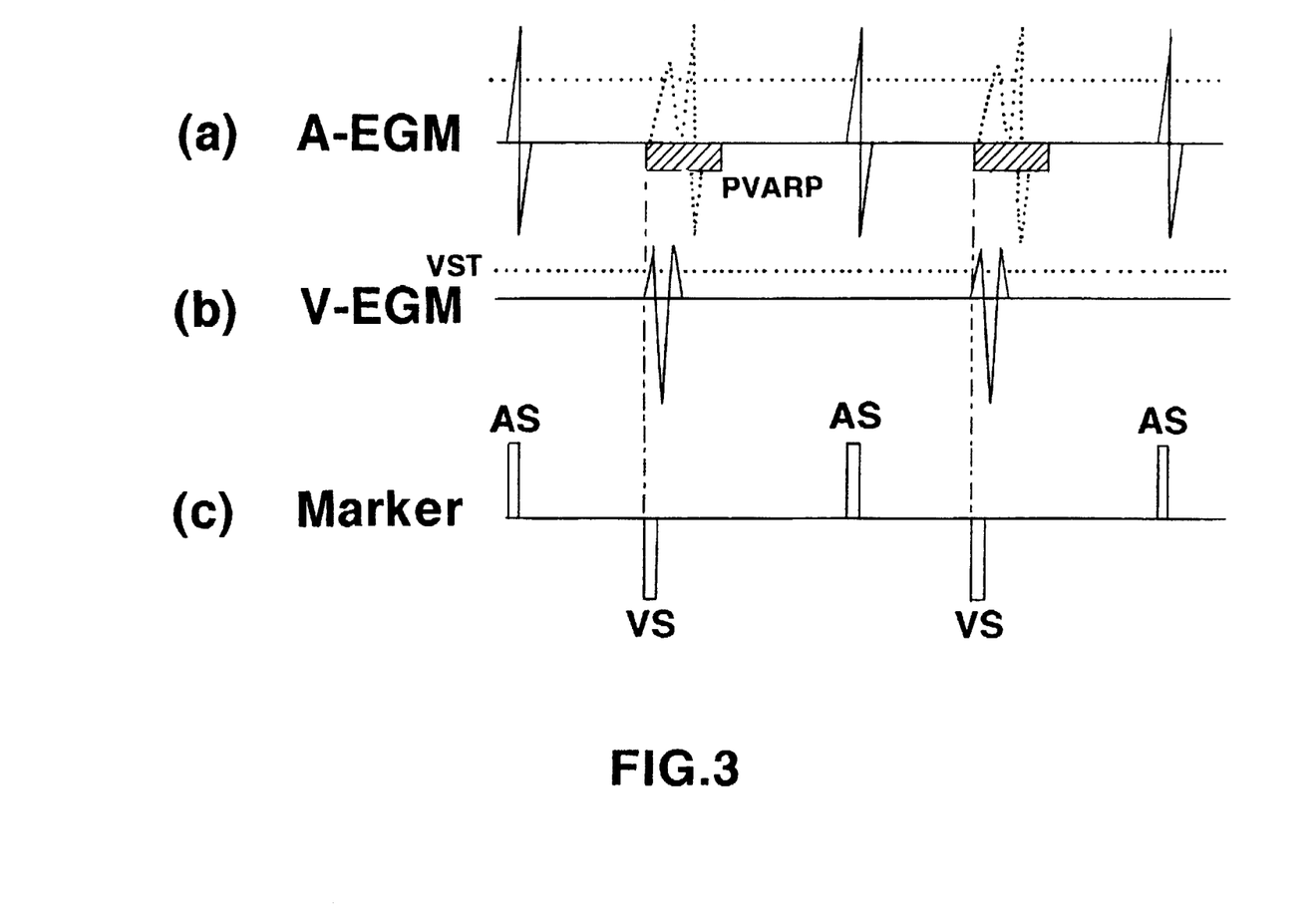
FIG. 3 illustrates an example of P-wave undersensing that can occur due to fusion beats where the P-wave is masked by a far field R-wave and the generation of a PVARP due to the V-SENSE from the V-EGM.

FIG. 3, by contrast, depicts an example of P-wave undersensing that can occur when ventricular depolarizations occur late in the intrinsic heart cycle at the time when an atrial depolarization is about to occur. The atrial and ventricular dissociation results in what is referred to as a "fusion beat". In tracing (a), the P-wave in the A-EGM is sensed as indicated by the AS marker in tracing (c). Then, the R-wave in the V-EGM is sensed as indicated by the VS marker in tracing (c). At that time, the ABP and PVARP is started, masking both the R-wave signal artifact and the P-wave signal at the input to the atrial sense amplifier 17 as shown in tracing (a). Although not specifically illustrated in FIG. 3, generation of atrial and ventricular pacing pulses can become erratic as a result of undersensing the intrinsic P-waves.

In such current implantable pacemakers, the blanking periods that are necessary to protect the sense amplifiers and the refractory periods that are used to provide noise detection and protection have minimum lengths that do not vary with pacing rate. Consequently, the use of such blanking and refractory periods can effectively blind the sense amplifiers during a substantial part of the cardiac cycle, particularly as the cardiac cycle shortens at high intrinsic atrial rates. While the V-A interval shortens, the delay until the far-field R-wave appears at the atrial electrodes and the width and amplitude of the far-field R-wave as observed at the atrial electrodes remains relatively constant, dictating constant ABP and PVARP intervals. Thus, the ABP and ARP intervals shorten the available time in the heart cycle for sensing legitimate P-waves.

Other approaches to distinguish P-waves from R-waves in a variety of contexts, including the use of adaptive filter algorithms or morphological "template matching" algorithms, have been suggested in the prior art. These approaches seek to either eliminate a waveform that is not of interest or to match an unknown waveform shape to a set of waveform shapes. They have been applied in practice to electrocardiograph (ECG) waveforms as they appear either from skin electrodes or recorded ECG tracings EGM signals and have been proposed for implantable cardiac monitors or stimulators.

Adaptive filter algorithms have been used in: 1) surface ECG signal analysis for fetal heart beat detection and 60 Hz noise cancellation as disclosed by B. Widrow et al. in "Adaptive Noise Cancellation: Principles and Applications", *IEEE Proc.* 1975; 63:1692–1716; 2) electroencephalogram (EEG) analysis for noise cancellation; 3) impedance pneumography analysis for cardiogenic artifact cancellation by Sahakian A. V. et al., "Canceling the Cardiogenic Artifact in Impedance Pneumography", *IEEE 17th ACEMB* 1985; 855–859; and 4) in a variety of approaches for effecting P-wave detection and discriminating P-waves from R-waves.

In this context, P-wave detection in the ECG signal employing adaptive filtering has been described by Zhu Yi-Sheng et al., in "P-Wave Detection by An Adaptive QRS-T Cancellation Technique", *IEEE Comp. Cardiol.* 1986; 249–252. A closely related approach, using the Least Mean Square (LMS) algorithm in the adaptive filter, is described by DuFault, R. A. et al. in "P-Wave Detection in the Surface ECG via the LMS Algorithm", *IEEE Comp. Cardiol.* 1986; 245–248 and in "Dual Channel P-wave Detection in the Surface ECG, Using the LMS Algorithm", in *IEEE, 8th ACEMB Proc.*, 325–328, as well as in U.S. Pat. No. 4,793,361. In these external ECG signal processing systems, the adaptive filtering of the ECG signal waveform is conducted to suppress the energy of the surface QRS signal in order to more readily detect the surface P-wave.

In a further U.S. Pat. No. 4,799,486 to DuFault et al., adaptive filtering is employed to suppress the far field R-wave in the A-EGM in an implantable dual chamber pacemaker of the type described above. The LMS algorithm is utilized for estimation of a transfer function as a means of discriminating between the P-wave and the far field R-wave or between tachyarrhythmias. The transfer function, once determined, generates a replica ("estimate") of the A-EGM, based on LMS filtering of the V-EGM. The estimate is subtracted from the A-EGM signal to produce a null or "error" signal, in the presence of stable rhythm whereby the far field R-wave is suppressed. This adaptive filtering algorithm is proposed for use in an implantable dual chamber pacemaker to eliminate or minimize refractory the ARP and PVARP.

In U.S. Pat. No. 4,799,493, a similar system is used to distinguish P-waves from R-waves in the A-EGM for detecting a tachyarrhythmia. In the '493 patent system, filters specifically tuned to produce null signals in the presence of sinus tachycardia or ventricular tachycardia are disclosed, as well as adaptive filters which automatically converge in the presence of stable rhythm. The automatically adapting filters are disclosed as capable of distinguishing between ventricular fibrillation and tachycardias, in that the LMS algorithms will not allow convergence in the presence of fibrillation. This technique is also described in the article "Dual Lead Fibrillation Detection for Implantable Defibrillators Via LMS Algorithm" by DuFault et al., published in *Computers and Cardiology* 1986, IEEE Computer Society Press, pp. 163–166.

In these applications of adaptive filters to the processing of the ECG and A-EGM, at each sampling step, a full length convolution is calculated and all filter coefficients are updated, requiring a great amount of processing overhead. This approach is not suitable to real time processing of the A-EGM in an implantable dual chamber cardiac stimulator or monitor.

Morphological algorithms, such as template matching, correlation analysis and area function algorithms, have been used for tachyarrhythmia analysis, or P-wave detection from intracardiac EGMs and surface ECGs. Various detection and discrimination schemes have been proposed to distinguish or classify tachyarrhythmias based on morphology as described for example by Throne, R. D. et al. in "A Comparison of Four New Time-Domain Techniques for Discriminating Monomorphic Ventricular Tachycardia from Sinus Rhythm Using Ventricular Waveform Morphology", *IEEE Trans. Biomed. Eng.* 1991; 38:561–570 and by Langberg, J. J. et al. in "Identification of Ventricular Tachycardia with Use of the Morphology of the Endocardial Electrogram", *Circulation* 1988; 77:1363:1369.

In addition, U.S. Pat. No. 5,086,772 to Larnard et al. discloses an implantable arrhythmia control system for recognizing and classifying bradycardia, normal rhythm, tachycardia, electrical interference and ventricular fibrillation and delivering an appropriate therapy, if necessary. In one of the approaches taken to classify a waveform, the variability of R-wave interval (rate), R-wave width, and polarity is monitored (optionally with P-wave detection and measurement of P-R interval and atrial rate in a dual chamber system) along with the morphology of the a windowed portion of the R-wave. The R-wave is sensed by an R-wave sense amplifier preferably coupled to a pair of bipolar ventricular electrodes. The R-wave sense amplifier output is continuously digitized, and a window running forward and backward in time is applied to the digitized data at R-wave peak detection. The windowed data is used in morphology analysis with respect to a stored normal sinus rhythm (NSR) template created in initialization of the device, presumably at implant, and periodically updated. The morphology characteristics are stated to be R-wave width and polarity at col. 5, lines 50–63, and are calculated in column 8, lines 8–25. These characteristics are determined for each detected R-wave, and the values are compared to thresholds related to the most recently stored NSR R-wave to distinguish between intact normal conduction beats and ectopic beats. The event classification of abnormal polarity and/or width increments an output event value to a "rhythm sum" in the rhythm classification algorithm.

In a different application directed to attaining atrial synchronous pacing benefits without an atrial sense electrode, Greenhut et al. propose a morphological system for detecting far field P-waves from a unipolar V-EGM derived from a standard ventricular electrode and remote electrode pair in the above-referenced article. The standard ventricular lead used in the reported experiments has closely spaced bipolar electrodes lodged in the ventricular apex. A unipolar V-EGM signal is sensed between one of the bipolar electrodes and a remote electrode, sampled and subjected to a template matching morphological analysis at each sample point. Simultaneously, a bipolar V-EGM signal is sensed between the bipolar electrodes, and the R-wave is detected therefrom in a standard peak detection operation. When the R-wave is peak detected, the preceding 50 ms. and the succeeding 200 ms. of sample values of the unipolar V-EGM signal are ignored or "blanked". In the remaining portion of the cardiac cycle less the 250 ms. period, P-waves are detected from the unipolar V-EGM by the template matching technique. The accuracy of P-wave detection was cross-checked from a surface ECG clearly showing the P-waves. The study was conducted with patients at rest, and limitations arising with the constraints presented by the limited computational power of an implantable system in real time in a full range of heart rates were not taken into account as noted by the authors.

In a comparison to the adaptive filtering techniques of DuFault et al. and Yi-Sheng et al., Greenhut et al. also concluded that adaptive filtering of the ECG or EGM will not produce a sufficiently clean signal from which P-waves can be detected by using conventional bandpass filtering and thresholding techniques, particularly when ectopic QRS complexes are present or the environment is quite noisy. As can be seen from the adaptive filter "error" output signals depicted in the '486 patent and the Yi-Sheng et al. article, the signal-to-noise ratio of the P-wave signal peaks compared to the residual signal levels is still relatively low after the QRS complex is removed.

Greenhut et al. also note that their proposed technique is not usable at moderate to high heart rates due to the 250 ms. blanking period or where fusion beats occur at lower rates. Greenhut et al. suggest that "At higher atrial rates, it may be possible to adaptively filter (subtract) [citing DuFault et al. and Zhu Yi-Sheng et al.] the QRST complex for improved P-wave detection by template matching methods" (p. 1301). Presumably, the suggested adaptive filtering would use the approach proposed by DuFault et al. shown in FIG. 2 of the '486 patent, for example where the "input" signal is the near field V-EGM, the "desired" signal is the unipolar A-EGM, and the "error" signal is subjected to the template matching method, rather than to the filtering and thresholding technique described by DuFault. If this substitution were made, the adaptive filtering processes and the morphology processes would be conducted at every sampling step with a full length convolution and an update for every filter coefficient. While this approach might theoretically overcome the limitations imposed by the 250 ms. blanking period, the resulting adaptive filtering and morphology analyses would be extremely costly in terms of computational time and complexity and difficult to implement in an implanted cardiac stimulator or monitor.

In summary, the key role of a morphology analysis is to identify a waveform, while the key role of an adaptive filter is to cancel an undesirable waveform. Historically, the adaptive filter algorithms and morphology algorithms have been individually used in various biomedical signal analyses. Many difficulties have been experienced with individual algorithms. As shown above, adaptive filtering of clinical ECG or EGM will not produce sufficiently clean signal from which a waveform can be surely detected by using conventional bandpass filtering and thresholding. And, direct use of a morphological algorithm for a waveform identification is very difficult when patient's hearts exhibit AV block and frequent fusion beats. The combination of the two techniques to the extent that it may have been suggested is computationally expensive and time consuming.

There is a therefore a need for a signal processing technique permitting sensing of the P-wave in the A-EGM throughout the entire cardiac cycle thereby substantially eliminating the need for the ARP and PVARP and reducing or substantially eliminating oversensing or undersensing. Moreover, there is a need for such a technique that is usable in an implantable cardiac stimulator or monitor that is not computationally complex so that the recognition of P-waves in the A-EGM can be accomplished in real time to control operations of the stimulator or monitor.

SUMMARY OF THE INVENTION

It is therefore an object of the present invention to provide a signal processing technique permitting sensing of the P-wave in the A-EGM throughout the entire cardiac cycle thereby substantially eliminating the need for the ARP and PVARP and reducing or substantially eliminating oversensing of far field R-waves or undersensing of P-waves particularly in fusion beats.

It is a further object of the present invention to provide such a technique that is usable in an implantable cardiac stimulator or monitor that is not computationally complex so that the recognition of P-waves in the A-EGM can be accomplished in real time to control operations of the stimulator or monitor.

It is yet a further object of the present invention to provide such a technique that ensures an accurate recognition of the P-Wave in the A-EGM from which operating modes of the implantable cardiac stimulator or monitor can be controlled.

The adaptive and morphological method and system of the present invention comprise two basic steps. In the first step, an adaptive filtering stage using an R-wave correlated reference (R-Trigger) that removes undesirable R-waves and high amplitude T-waves from the A-EGM signal. The use of R-wave time position sequence or higher order sequence as the reference input signal in the adaptive filter stage significantly enhances the processing speed.

In the second step, morphology analysis of the adaptively filtered A-EGM is conducted to detect the P-waves in the adaptive filter output error signal only when atrial channel trigger (P/R-Trigger) signals are detected in the A-EGM. This reduces the amount of time that morphology computation is conducted in the cardiac cycle, thereby reducing computational complexity and allowing real time analysis of the A-EGM in an implantable cardiac stimulator or monitor.

These objects and features of the present invention are realized in a system of the type having at least an atrial sense amplifier coupled with an atrial sense electrode for placement in relation with an atrium for detecting the atrial electrogram and a ventricular sense amplifier coupled with a ventricular sense electrode for placement in relation with a ventricle for detecting the ventricular electrogram. A method and apparatus for processing a sensed atrial electrogram in conjunction with a sensed ventricular electrogram to accurately distinguish atrial P-waves from far field ventricular events, including far field R-waves and to avoid oversensing such far field ventricular events as atrial sense events and undersensing atrial events occurring within a fusion beat masked by a far field ventricular event in the atrial electrogram is provided. Atrial channel trigger signals are generated in response to sensed P-waves and far field R-waves in the atrial electrogram, and ventricular channel trigger signals are generated in response to sensed R-waves in the ventricular electrogram. In response to each ventricular channel trigger signal, the sensed atrial electrogram signal is adaptively filtered for an adaptive filter time window only to remove the far field R-wave signal from the sensed atrial electrogram signal while avoiding adaptive filtering of the sensed atrial electrogram signal at other times. In response to each atrial channel trigger signal, the adaptively filtered, sensed atrial electrogram signal is subjected to a morphological analysis with respect to a morphological model of a P-wave only during a morphology time window. In this manner, P-waves in the sensed atrial electrogram signal are detected and far field R-waves in the sensed atrial electrogram signal are not mistakenly detected as P-waves, while morphological analysis of the sensed atrial electrogram at other times is avoided.

The generation of the atrial channel trigger signal and the ventricular channel trigger signal is accomplished by the steps of and means for: establishing an atrial sense criterion; comparing the sensed atrial electrogram signal to the atrial sense criterion and deriving an atrial event trigger signal each time a sensed atrial electrogram signal characteristic satisfies the atrial sense criterion; establishing a ventricular sense criterion; and comparing the sensed ventricular electrogram signal to the ventricular sense criterion and deriving a ventricular event trigger signal each time a sensed ventricular electrogram signal characteristic satisfies the ventricular sense criterion.

The present invention is preferably implemented in the context of a dual chamber cardiac medical device of the type having at least an atrial sense amplifier coupled with an atrial sense electrode for placement in relation with an atrium for detecting the A-EGM and a ventricular sense amplifier coupled with a ventricular sense electrode for placement in relation with a ventricle for detecting the V-EGM, wherein a method of and apparatus for discriminating atrial P-waves from far-field ventricular R-waves both appearing in the A-EGM are implemented comprising the steps of and means for: sensing the A-EGM from the atrial sense electrode, the A-EGM including the P-waves and far field R-waves conducted into the atria from the ventricle; sensing the V-EGM from the ventricular sense electrode, the V-EGM including the R-waves in the ventricle; generating P/R-Trigger signals in response to P-waves and far field R-waves in the A-EGM; generating R-Trigger signals in response to R-waves in the V-EGM; synchronizing the timing of generation of the R-trigger signal to a corresponding P/R-Trigger signal; adaptively filtering the A-EGM signal by applying the R-Trigger signal to the input of an adaptive filter and combining the A-EGM signal with the output signal of the adaptive filter to which combined error signal is applied as a feedback signal to thereby derive the error signal representing the A-EGM signal in which the far field R-wave is adaptively canceled; providing a morphological model of a P-wave in the A-EGM; and upon the occurrence of each P/R-Trigger signal, establishing a morphology window and template matching the error signal to the morphological model of the P-wave in the A-EGM only during the morphology window, whereby only P-waves in the error signal are found to match the morphological model and are distinguished from residual noise signals in the error signal.

The ability to discriminate far-field R-waves from P-waves in the A-EGM in accordance with the present invention is believed to be a major attribute for avoiding improper atrial oversensing and undersensing, and may be used to enhance detection of auto-capture in the ventricle, improve pacing mode switching reliability, simplify the DDD pacing algorithm, and extend the pacing therapy for hypertrophic cardiomyopathy (HCM) patients who normally have extraordinarily large amplitude far field R-waves in the A-EGM.

Moreover, either the adaptive filter algorithm or a morphological algorithm has only been applied to intrinsic surface ECGs and intrinsic intracardiac EGMs, but not paced EGMs. The method and apparatus of the present invention can be used for real time discrimination of both intrinsic and paced EGMs as well as surface ECGs of pace driven cardiac events.

In addition, a wide variety of morphological functions can be used in the morphological analysis. These new functions include contrasted correlation-differential area function, contrasted area-differential area function and contrasted correlation-area function that provide enhanced detection performance in noise-contaminated signals.

In implantable arrhythmia control devices, the ability to discriminate far field R-waves from P-waves in real time can provide the foundation for accurate and rapid determination of atrial arrhythmias or ventricular arrhythmias using any of the known arrhythmia detection criteria. In implantable cardiac monitors, the discrimination may be used to ensure that the stored data is accurate.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

The preferred embodiment of the present invention is preferably implemented in a DDD or DDDR pacemaker of the type depicted in FIG. 1 or in any other implantable cardiac stimulator or monitor of the types described above that requires the detection and accurate discrimination of P-waves from R-waves for diagnostic or therapeutic purposes. Consequently, for each such application, at least the atrial and ventricular leads 12 and 9 and respective atrial and ventricular sense amplifiers 17 and 19 can be used for sensing the A-EGM and V-EGM, and the logic and timing circuit 20 can be used to distinguish the P-waves from the R-waves in the manner described below.

When the IPG 14 of FIG. 1 is provided with both atrial and ventricular sense amplifiers, it may be programmed or designed with an algorithm for operating in several pacing modes that generally involve using the sensed P-wave to time at least the delivery of a V-PACE pulse by a ventricular pacing pulse generator 18 after an A-V delay unless an R-wave is sensed by the ventricular sense amplifier 19 before time-out of the A-V delay. In the DDDR pacing system depicted in FIG. 1, the IPG 14 is also provided with a logic and timing circuit 20 for setting and timing out the A-V delay and also setting and timing out a V-A escape interval starting on delivery of a ventricular pace pulse or sensing of an R-wave by ventricular sense amplifier 19. The V-A escape interval is itself terminated either by a P-wave sensed by atrial sense amplifier 17 before it times out or delivery of an A-PACE pulse by the atrial pacing pulse generator 16 on time-out.

The logic and timing circuit 20 establishes a V-V rate governing the setting of the V-A escape interval that may itself vary depending on a physiologic signal derived from a physiologic sensor, e.g. a patient activity sensor 21, in a manner well known in the art. To the extent that the intrinsic atrial heart rate exceeds the current V-V rate, the recurring P-waves are sensed and control the synchronous pacing rate up to an upper pacing rate limit.

The well known DDD and DDDR pacing mode thus encompasses atrial and ventricular pacing and sensing and operation in either a synchronous or an inhibited manner depending on the prevailing atrial and ventricular heart rhythm. The related VDD pacing mode provides atrial synchronous, ventricular inhibited pacing, i.e., the DDD pacing mode as described above, but without the atrial pacing capability. In both the DDD and VDD pacing modes, the ability to sense P-waves and distinguish them from R-waves is crucial to avoid inappropriate resetting of V-A escape intervals and/or triggering of synchronous ventricular pacing. In accordance with the present invention, the ARP and PVARP may be shortened considerably to allow more accurate detection of P-waves and R-waves at higher intrinsic heart rates. The ABP and VBP are retained in such implanted systems providing pacing in at least one of the chambers. The incidences of undersensing and oversensing are reduced.

Figure 4:
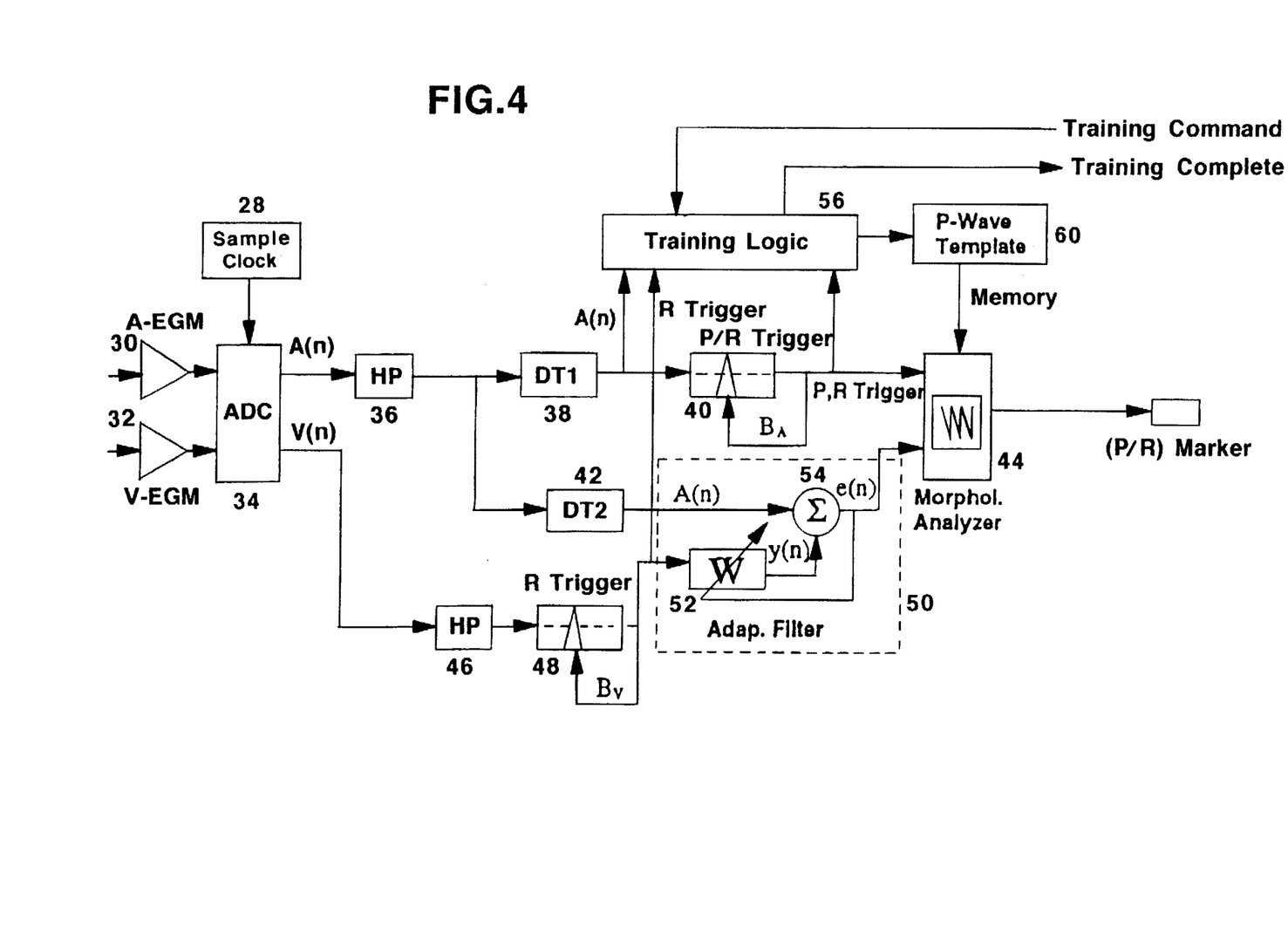
FIG. 4 is a simplified schematic illustration of one preferred embodiment of the present invention that may be implemented in the logic and timing circuit 20.
Figure 5:
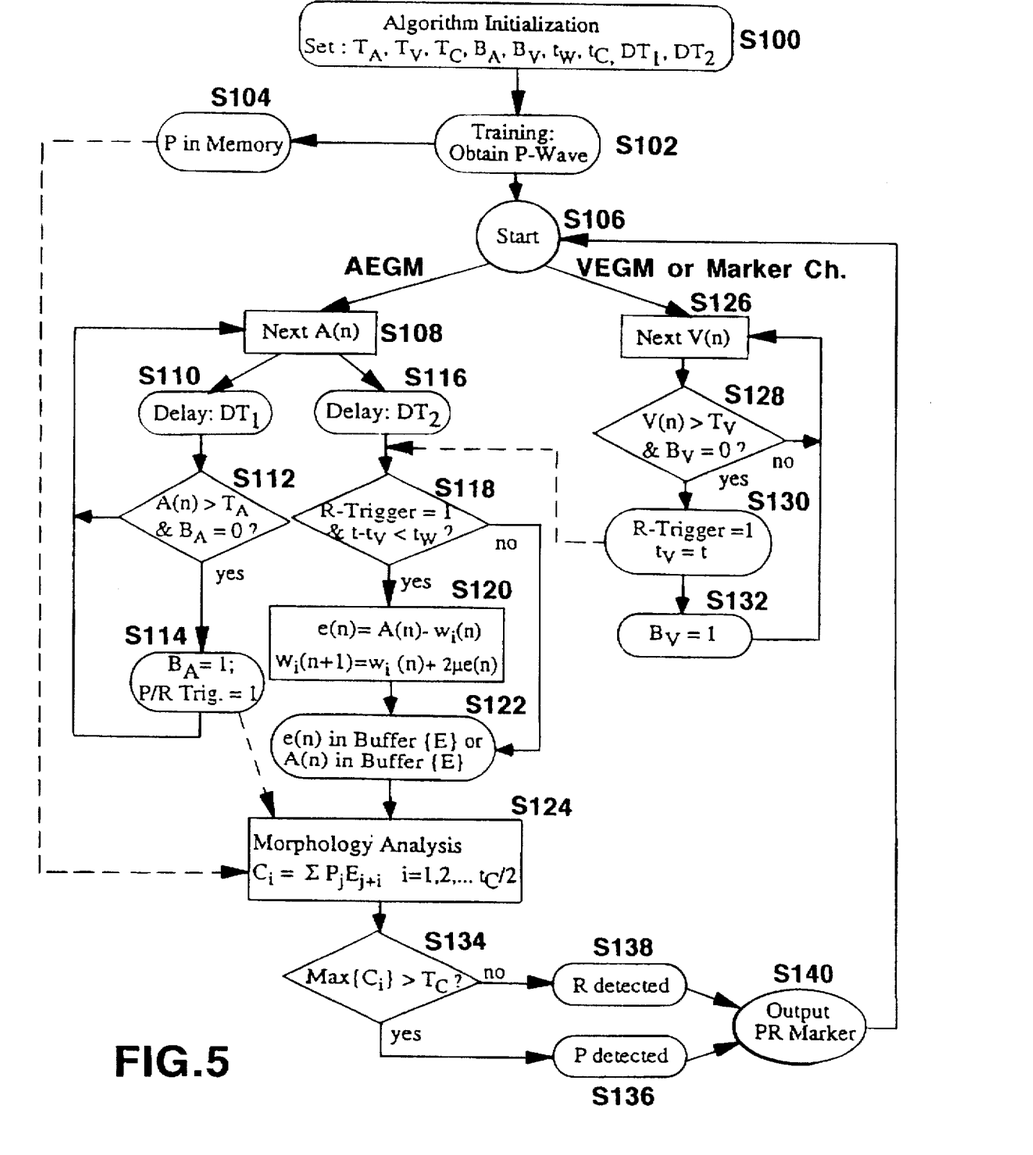
FIG. 5 is a flow chart of the operation of one preferred embodiment of the present invention.

The overall architecture of the adaptive filter and morphology system of the present invention is illustrated in the digital signal processing block diagram shown in FIG. 4 that operates in the manner of the flow chart of FIG. 5. In FIG. 4, the analog A-EGM is processed in the atrial sense amplifier stage 30, and the analog V-EGM is processed in the ventricular sense amplifier stage 32 which may be initial stages of the conventional analog signal atrial and ventricular sense amplifiers 17 and 19, respectively. In the pacing context, or in the case of a PCD system where pacing and/or high voltage shock therapies are delivered, the inputs to the amplifier stages 30 and 32 may be disconnected from the atrial and ventricular leads in response to and for the durations of the respective ABPs and VBPs which are typically on the order of 10–12 ms following delivery of pacing pulses.

Certain of the remaining components of the system illustrated in FIG. 4 may be incorporated into the atrial and ventricular sense amplifiers. However, for simplification, it is assumed that they are incorporated for the most part in logic and timing circuit 20. In an actual implementation, the system of the present invention may be substituted for the remaining stages of the conventional atrial and ventricular sense amplifiers 17 and 19. The P-Markers and R-Markers that are derived from the A-EGM digital processing in FIGS. 4 and 5 can be used instead of the A-SENSE event signals and offer the advantage of signifying the nature of the event. The R-Marker derived from the V-EGM digital peak detection processing in FIGS. 4 and 5 may be used as the V-SENSE event signal. It is possible however, to retain the analog sense amplifiers and provide the A-SENSE and V-SENSE event signals in parallel with the P-Marker and the R-Marker signals.

The amplified and filtered analog A-EGM and V-EGM signals are digitized in ADC 34 at a sampling frequency of 256 Hz., for example, or about every 4 ms. established by sampling clock 28. It will be understood that the digitized sample values A(n) and V(n) are processed with a sampling step time tag appended to each value that is used for timing certain periods as described below. The A(n) sample value is high pass filtered preferably at 1.0 Hz in high pass filter 36 to remove any baseline drift in the signal level and is then applied to a first delay 38. The delayed A(n) sample value is applied to an atrial sense threshold comparator 40, where the A(n) sample value is compared to an atrial sense threshold level. The atrial sense threshold level is adapted to be programmed low enough to ensure that the A(n) sample values signifying P-waves always exceed it. In so doing, the far field R-waves of the same or greater amplitude will also exceed the atrial sense threshold. In each case, a P/R-Trigger pulse or state of about 4 ms in duration is generated and is applied to a trigger input terminal of the morphology analyzer 34 to trigger it into operation for a prescribed comparison time window as described below. The atrial sense threshold comparator 40 is digitally "blanked" following the generation of the P/R-Trigger for a programmable atrial trigger blanking interval $B_A$ of about 100 ms to prevent multiple triggering by successive A(n) sample values exceeding the atrial sense threshold.

The digitized V-EGM signal V(n) sample value is also high pass filtered at preferably 1.0 Hz by a further high pass filter 46 to remove signals contributed by baseline signal drift, and the filtered V(n) sample value is applied to a ventricular sense threshold comparator 48. The amplitude of the A(n) sample value is compared to a ventricular sense threshold level. The ventricular sense threshold is adapted to be programmed high enough to ensure that the V(n) sample values derived from the R-wave always exceed it and so that V(n) sample values representing the amplitudes of any far field P-waves or any T-waves do not exceed it. When the V(n) sample value exceeds the ventricular sense threshold in ventricular sense threshold comparator 48, an R-Trigger pulse is generated. The R-Trigger pulse duration is also on the order of about 4 ms or one 256 Hz. clock period. The ventricular sense threshold comparator 48 is therefore also digitally blanked following the generation of the R-Trigger for a programmable ventricular trigger blanking interval $B_V$ of about 100 ms to prevent multiple triggering by successive V(n) sample values derived from a single R-wave exceeding the ventricular sense threshold.

Because of the disparity in the atrial and ventricular sense thresholds, the atrial sense threshold comparator 40 is likely to generate a P/R-Trigger earlier than the ventricular sense threshold comparator 48 generates an R-Trigger for the same R-wave. To ensure substantially simultaneous or synchronous triggering of the R-Trigger and P/R-Trigger in response to a single ventricular event, the first delay 38 is programmed to a delay interval $DT_1$ that delays the generation of the P/R-Trigger. The high pass filtered and digitized A(n) sample is also applied to a second delay circuit 42 which delays it a second delay $DT_2$ so that the P/R-Trigger and the R-Trigger signals occur first and substantially simultaneously before the A(n) sample is processed through the adaptive filter 50 generating the error signal e(n) and the output or estimate signal y(n) as described below. The allows the morphology analyzer to be triggered by the P/R-Trigger to commence the morphology analysis for a set period of time $t_C$ as the error signal e(n) is received and for the error signal e(n) to only represent the P-wave of interest.

The high pass filtered and delayed A-EGM sample A(n) and the undesired estimate signal y(n) are applied to first and second terminals of the adaptive filter summation block 54. The resulting error signal e(n) includes the "interested signal" A(n) sample values related to the P-wave, with the far field R-wave and possibly the T-wave significantly reduced in value. The R-Trigger impulse is applied as an input signal or reference vector to an M-tap delay line digital filter 52 wherein the M tap values or coefficients are determined by an adaptive algorithm. The R-trigger impulse signifies which of the digital filter 52 coefficients is to be updated, and the digital filter 52 is updated one filter coefficient per sample clock period. The overall goal of the adaptive filter 50 is to minimize the mean square error between the digital filter 52 output or estimate signal y(n) and the delayed A-EGM in the error output e(n). The LMS adaptive algorithm described in the above-referenced DuFault et al. and Yi-Sheng et al. patents and articles is used in this study for its robust characteristics and simplicity. However, in the present invention, the adaptive algorithm is only triggered by an R-Trigger, significantly reducing computations. The LMS update scheme is written as the following equations:

$$y(n) = \sum_{k=0}^{k=M-1} w_k(n)x(n-k) \quad (1)$$

$$e(n) = d(n) - y(n) \quad (2)$$

$$w_k(n+1) = w_k(n) + \mu e(n)x(n-k) \quad (3)$$

where e(n) is the error signal output of the adaptive filter 50, y(n) is the output of the M-tap digital filter 52, $w_k(n)$ is the kth digital filter 52 coefficient at time n, d(n) is the delayed A(n) sample at n.x(n−k) is the kth previous reference input, and μ is the adaptation constant. The adaptation constant μ controls the speed of adaptation and how closely the adaptive filter 50 approaches the optimum filter. Again referring to FIG. 4, the R-Trigger impulse generated from the V-EGM is used as the input or reference vector x(n) to the digital filter 52 to reduce the number of multiplication operations needed to be performed in Equation (1). If the ventricular sense threshold detector 48 was triggered three samples previously, the reference vector at the nth sampling step (t=n) is:

$$x(n) = [0, 0, 0, 1, 0, \ldots, 0] \quad (4)$$

In general, if the R-trigger impulse was generated p samples previously, Equations (1–3) will reduce to:

$$y(n) = \sum_{k=0}^{k=M-1} w_k(n)x(n-k) = w_{-p}(n) \quad (5)$$

$$e(n) = d(n) - w_p(n) \quad (6)$$

$$w_p(n+1) = w_p(n) + \mu e(n) \quad (7)$$

Only the pth coefficient $w_p(n)$ is updated at the nth time step. The adaptive filter coefficients are updated as the impulse shifts through the delay line forming the digital filter 52. This LMS implementation requires 2M multiplication operations for filtering each beat of A-EGMs where M is the number of adaptive filter taps.

As described above, the error output signal e(n) is still noisy due to residue from the incomplete removal of the QRS complex. The P-wave signal amplitudes and frequency components may be close to the noise signal amplitudes and frequency components may be comparatively close, making the classic filtering and amplitude comparison discrimination still unreliable. Advantageously, the P-wave masked by the far field R-wave within a fusion beat is exposed. In order to complete the discrimination of P-waves from far field R-waves, the correlation between the adaptive filter output and a saved P-wave template is estimated in morphology analyzer 44. To improve the computation efficiency, the estimate is performed only each time that the P/R-Trigger is generated signifying that the A-EGM amplitude is greater than the atrial sense threshold. As set forth below, the estimate is performed employing one of a variety of morphology discrimination algorithms in comparison with a unit norm template formed of an averaged P-wave template obtained from the A-EGM in a training regimen. The correlation estimate $C_{e,s}$ between the unit norr template and the adaptive filter error output signal e(n) is:

$$c_{es}(n) = \sum_{k=0}^{k=t_C-1} e(n-k)s(k) \qquad (8)$$

where s(k) is the kth sample of the P-wave template, $t_C$ is the time window for morphology analysis, and e(n−k) is the kth delay of the adaptive filter output at time n. Discrimination between the P-wave and far field R-wave is accomplished by comparing correlation estimate $c_{e,s}$ (n) to a programmed threshold value $T_C$. If $c_{e,s}$ (n) is greater that $T_C$, the correlation estimate conducted in morphology analyzer 44 outputs a P-Marker. Otherwise morphology analyzer 44 outputs an R-Marker because of coincidence with the R-Trigger.

The use of a morphology function essentially requires the knowledge of a P-wave template maintained in template memory 60 that is unique for each patient. Automatic training of the algorithm is employed in the present invention in training logic 56 to derive the P-wave template and store it in the template memory 60 for comparison to the error signal e(n) at each P/R-Trigger within the time window $t_C$. The P-wave waveform model of the patient is obtained automatically in the first few cardiac cycles of the A-EGM. In the first few cardiac cycles, non-overlapping P-waves are automatically identified based on the timing of R-Trigger and P/R-Trigger pulses applied to training logic block 56. The non-overlapping A(n) samples in the sample windows centered to the non-overlapping P/R-Trigger time are averaged to serve as the template for morphology processor 44 and stored in template memory 60. This same training approach can also be used to adaptively update the template memory 60 for a patient during his/her different activity levels.

A variety of morphology discrimination algorithms may be employed in the comparison of the error output signal e(n) with the P-wave template including the following wherein $\{f_k\}$ is the morphological function, $\{S_i\}$ is the signal to be processed, k is the sample number corresponding to (n), $\bar{S}_k$ is the mean of $\{S_k, S_{k+1}, S_{k+2}, \ldots S_{k+T}\}$, $\{V_i\}$ is the template of the P-wave, $\bar{V}$ is the mean of the template $\{V_i\}$, and T is the time window of the morphology template ($t_C$ above and below):

1) Area Function $$f_k = \sum_{i=1}^{T} |S_{i+k}| \quad k=1,2,3,\ldots,T$$

2) Correlation Function $$f_k = \sum_{i=1}^{T} (S_{k+i} - \bar{S}_k)(V_i - \bar{V})/T^2 \quad k=1,2,3,\ldots,T$$

3) Differential Area Function $$f_k = \sum_{i=1}^{T} |(S_{k+i} - \bar{S}_k) - (V_i - \bar{V})|/T \quad k=1,2,3,\ldots,T$$

4) Bin-Area Correlation Function $$f_k = \sum_{j=1}^{\frac{T}{M}} \left\{ \sum_{i=1}^{M} (S_{k+(j-1)\times M+i} - \bar{S}_k) \cdot \sum_{i=1}^{M} (V_{(j-1)\times M+i} - \bar{V}) \right\} /T$$

$$k=1,2,3,\ldots,T$$

5) Bin-Area Differential Area Function $$f_k = \sum_{j=1}^{\frac{T}{M}} \left| \sum_{i=1}^{M} (S_{k+(j-1)\times M+i} - \bar{S}_k) - (V_{(j-1)\times M+i} - \bar{V}) \right|/T$$

$$k=1,2,3,\ldots,T$$

6) Contrasted Correlation-area Function $$f_k = \frac{\sum_{i=1}^{T} (S_{k+i} - \bar{S}_k)(V_i - \bar{V})}{\sum_{i=1}^{T} |S_{i+k}|} \quad k=1,2,3,\ldots,T$$

7) Contrasted Correlation-Differential Area Function $$f_k = \frac{\sum_{i=1}^{T} (S_{k+i} - \bar{S}_k)(V_i - \bar{V})}{\sum_{i=1}^{T} |(S_{k+i} - \bar{S}_k) - (V_i - \bar{V})|} \quad k=1,2,3,\ldots,T$$

8) Contrasted Area-Differential Area Function $$f_k = \frac{\sum_{i=1}^{T} |S_{i+k}|}{\sum_{i=1}^{T} |(S_{k+i} - \bar{S}_k) - (V_i - \bar{V})|} \quad k=1,2,3,\ldots,T$$

FIG. 5 depicts a flow chart illustrating the steps of carrying out the method of the present invention. At step S100, the parameters for the algorithm, including the atrial and ventricular thresholds $T_A$, $T_V$, the morphology analysis threshold or correlation ratio $T_C$, the atrial and ventricular sense threshold comparator blanking periods $B_A$, $B_V$, the time window or length (number of taps) $t_w$ of the adaptive filter, and the delay times $DT_1$, $DT_2$. The time window $t_w$ is selected to be at least as wide as the width of the far field R-wave in the A-EGM. In steps S102 and S104, the training routine is conducted to obtain the P-wave template and store it in template memory 60 for use in the morphology analysis in step S124. At step S106, the detection and discrimination algorithm is commenced for each heart cycle.

The A-EGM and V-EGM signal processing, including sampling and ADC into digitized A(n) and V(n) sample values, is conducted in parallel, real time operations as shown in FIG. 4, and, for convenience, the A-EGM channel processing is first described. At step S108, the next A(n) sample is obtained, and in parallel operations as shown in FIG. 4, the sample A(n) is delayed by delay times $DT_1$ and $DT_2$ in steps S110 and S116. At step S112, following step S110, the delayed A(n) sample value is compared to the atrial sense threshold $T_A$. If it exceeds it, and if the blanking period $B_A$ is not timing out, then a P/R-Trigger is generated, and the atrial sense threshold comparator blanking period $B_A$ is started in step S114. Then, the P/R-Trigger is provided to the morphology analyzer in step S122 to trigger the morphology analysis of the error signal e(n) during the time window $t_c$ as described below. Otherwise, the next sample A(n) is awaited in step S108.

In step S118, following the time out of the second delay $DT_2$ in parallel step S116, the determination is made whether the R-Trigger is currently being generated by ventricular sense threshold comparator 48 and if the time window $t_w$ has not timed out. Turning to steps S126–S132, the R-Trigger is generated in step S130 upon the occurrence of a V(n) sample value in step S126 that has an amplitude exceeding the ventricular sense threshold $T_V$ and if the ventricular sense threshold comparator blanking period $B_V$ is not timing out. Until this occurs, the V(n) samples are disregarded in steps S126 and S128. When these conditions are satisfied in step S128, the R-Trigger is generated and a time marker $t_v$ is set to the current time $t_i$ in step S130. The ventricular sense threshold comparator blanking period $B_V$ is then set in step S132, and the analysis of the next V(n) sample is commenced in step S126.

Returning to step S118, when the R-Trigger is present and the time conditions of step S130 are satisfied, then the conditions of step S118 are tested. When the R-Trigger occurs, it is applied to the reference vector to digital filter 52 in FIG. 4 as described above. During the time $t-t_v<t_w$, the error function e(n) is estimated according to the formulae:

$$e(n)=A(n)-W_j(n)W_j(n+1)=W_j(n)+2 \mu e(n)$$

where e(n) is the estimated error function and $W_i$ is the i(th) coefficient of the adaptive filter 52. Then, the e(n) error function sample value is placed in buffer {E} in step S122 for morphology analysis in step S124 when a P/R-Trigger occurs in step S114.

As long as the conditions of step S118 are not met, then the e(n) sample values correspond to the A(n) sample values entering the adaptive filter summation block 54 and these sample values pass into and through buffer {E} in step S122. The buffer {E} operates on a FIFO basis, and holds a number of samples (about twice as many as the number of samples appearing in the morphology window $t_C$), so that the A(n) sample values that are processed when the A-EGM signal levels are low or at baseline, pass out of buffer {E} and are not subjected to the morphological analysis in step S124.

The P/R-Trigger is generated in steps S110–S114 upon the occurrence of an A(n) sample value in step S126 that has an amplitude exceeding the atrial sense threshold $T_A$ and if the atrial sense threshold comparator blanking period BA is not timing out. Until this occurs, the A(n) sample values are disregarded in steps S110 and S112. When these conditions are satisfied in step S112, the P/R-Trigger is generated and a time marker $t_A$ is set to the current time $t_i$ in step S113. The atrial sense threshold comparator blanking period $B_A$ is then set in step S114, and the analysis of the next A(n) sample is commenced in step S108.

In this example, any one of the above listed morphological analysis algorithms can be used in step S124 to perform the template matching or correlation between the A(n) reference sample values of a reference P-wave in template memory stored in step S104 and the E(n) error function or A(n) sample value set present in buffer {E} when the P/R-Trigger occurs. In step S124, P is the template in the memory, $P_j$ is a sample value of the template, $E_{j+i}$ is the corresponding sample value in the E buffer aligned by a selectable shift value i=1, 2, 3 . . . to achieve a maximal correlation ratio. The programmable correlation window $t_C$ is set to include a number of sample values correlated with the width of the P-wave in the A-EGM. A series of correlation coefficients that are summed in the morphology algorithm in block S124 provide the correlation coefficient $C_i$ that is saved in a further buffer {C}. A maximum correlation value Max {$C_i$} is determined from among the $C_i$ coefficients that are saved in buffer {C}. In step S134, the Max {$C_i$} is compared to the programmed correlation ratio $T_C$. If Max {$C_i$}>$T_C$, then a P-wave is detected in step S136, and if Max {$C_i$}<$T_C$, an R-wave is detected in step S138. The resulting P-Marker or R-Marker is set in step S140, and the various time windows are reset and the detection algorithm is restarted in step S106.

The present invention was tested in real time on human subjects. To facilitate DSP programming and code development, we used a MATLAB™ and SIMULINK™ based code development environment, plus dSPACE to write, compile and down load the algorithm code, and monitor the algorithm operation and its inputs and outputs. MATLAB™ and SIMULINK™ are software products sold by ™ The MathWorks, Inc., Natick, Mass., USA. dSPACE tools are sold by dSPACE GmbH of Germany. The real time DSP adaptive morphology algorithm was implemented on a DS1102 DSP board provided by dSPACE GmbH, 33100 Paderborn, Germany which utilized a TMS320C31 DSP chip manufactured by Texas Instruments, Austin, Tex., USA.

A number of unipolar and bipolar electrode A-EGMs and V-EGMs were collected acutely during initial pacemaker implantation or replacement procedures or during EP study procedure. The A-EGMs and V-EGMs were isolated and amplified with an amplifier HIS2000 or HIS4000 (Madaus Schwarzer, Inc., Munich, German), or an EforM amplifier (Honeywell, Inc. Minneapolis, Minn., USA), or an in-house constructed biological signal amplifier (Medtronic, Inc., Minneapolis, Minn., USA). The amplified EGMs and the real time DSP detection outputs were simultaneously recorded on a TEAC RD 130 data recorder (TEAC Corp., Montebello, Calif., USA). The recorded EGM and the P-Marker and R-Marker channels were visually examined later to verify the real time detection analysis for each patient. The results of the tests showed a high degree of success in detecting P-waves in the A-EGM despite the presence of high amplitude far field R waves in the A-EGM.

The present invention may be employed in a variety of cardiac monitoring and therapy providing systems as stated at the outset. In one variation, the signal processing method and apparatus as described above with respect to FIGS. 4 and 5 may be substituted for the atrial and ventricular sense amplifier comparator stages typically incorporated into hybrid circuit sense amplifiers such that the resulting P-Marker and R-Marker signals are used instead of A-SENSE and V-SENSE event signals. In a hybrid combination, the atrial channel A-EGM processing may be conducted using the algorithm of the present invention, but the traditional ventricular channel V-EGM sense amplifier may be used to generate a V-SENSE event signal that is used as the R-Trigger signal applied as the reference vector to the adaptive filter 50.

The resulting R-Marker and P-Marker signals may be used to trigger or inhibit pacing operations in a dual chamber pacing mode or used in any of the known tachyarrhythmia detection algorithms referred to above to quickly determine whether or not an atrial or a ventricular tachyarhythmia is present.

To the extent that the approach of Greenhut et al. is realizable in practice, the present invention may also be employed to discriminate the P-wave from the R-wave in the EGM sensed across the ventricular ring and remote sense electrodes as suggested therein overcome the practical limitations described above.

The present invention is described above in the context of a multi-programmable, microcomputer based logic and timing circuit 20 with the filtering, timing, comparison, adaptive filtering and morphological functions conducted under the control of algorithms stored in memory. However, the present invention may also be usefully practiced in all such configurations by means of a full custom integrated circuit in each case. For example, such a circuit may take the form of a state machine in which a state counter serves to control an arithmetic logic unit to perform calculations according to a prescribed sequence of counter controlled steps.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

We claim:

1. A method of processing a sensed atrial electrogram in conjunction with a sensed ventricular electrogram to accurately distinguish atrial P-waves from far field ventricular events, including far field R-waves and to avoid oversensing such far field ventricular events as atrial sense events and undersensing atrial events occurring within a fusion beat masked by a far field ventricular event in the atrial electrogram, comprising the steps of:

generating atrial channel trigger signals in response to sensed P-waves and far field R-waves in the atrial electrogram;

generating ventricular trigger signals in response to sensed R-waves in the ventricular electrogram;

in response to each ventricular channel trigger signal, adaptively filtering the sensed atrial electrogram signal for an adaptive filter time window only to remove the far field R-wave signal from the sensed atrial electrogram signal while avoiding adaptive filtering of the sensed atrial electrogram signal at other times; and in response to each atrial channel trigger signal, subjecting the adaptively filtered, sensed atrial electrogram signal to a morphological analysis with respect to a morphological model of a P-wave only during a morphology time window, wherein P-waves in the sensed atrial electrogram signal are detected and far field R-waves in the sensed atrial electrogram signal are not mistakenly detected as P-waves, while avoiding morphological analysis of the sensed atrial electrogram at other times.

2. The method of claim 1, wherein the step of generating atrial trigger signals further comprises:

establishing at least one atrial sense criterion;

comparing the sensed atrial electrogram signal to the atrial sense criterion and deriving an atrial channel trigger signal each time a sensed atrial electrogram signal characteristic satisfies the atrial sense criterion.

3. The method of claim 1, wherein the step of generating ventricular trigger signals further comprises:

establishing at least one ventricular sense criterion;

comparing the sensed ventricular electrogram signal to the ventricular sense criterion and deriving a ventricular channel trigger signal each time a sensed ventricular electrogram signal characteristic satisfies the ventricular sense criterion.

4. The method of claim 1, further comprising the step of:

synchronizing the timing of generation of the ventricular trigger signal to a corresponding atrial trigger signal.

5. The method of claim 1, incorporated into a system of the type having at least an atrial sense amplifier coupled with an atrial sense electrode for placement in relation with an atrium for detecting the atrial electrogram and a ventricular sense amplifier coupled with a ventricular sense electrode for placement in relation with a ventricle for detecting the ventricular electrogram, a method of discriminating atrial P-waves from far-field ventricular R-waves, both appearing in the atrial electrogram, the method further comprising the steps of:

sensing the atrial electrogram from said atrial sense electrode, the sensed atrial electrogram signal including the P-waves and far-field R-waves; and sensing the ventricular electrogram from said ventricular sense electrode, the sensed ventricular electrogram signal including R-waves.

6. In a dual chamber cardiac medical device of the type having means for detecting the atrial electrogram (A-EGM) and means for detecting the ventricular electrogram (V-EGM), a method of discriminating atrial P-waves from far-field ventricular R-waves, both appearing in the A-EGM and to avoid oversensing such far field R-waves as P-waves and undersensing P-waves occurring within a fusion beat masked by a far field R-wave comprising the steps of:

generating atrial channel trigger (P/R-Trigger) signals in response to P-waves and far field R-waves in the A-EGM;

generating ventricular trigger (R-Trigger) signals in response to R-waves in the V-EGM;

upon the occurrence of each R-Trigger signal, adaptively filtering the A-EGM signal by applying the R-Trigger signal to the input of an adaptive filter and combining the A-EGM signal with the output signal of the adaptive filter to which a combined error signal is applied as a feedback signal to derive the error signal representing the A-EGM signal in which the far field R-wave is adaptively canceled only during an adaptive filter time window;

providing a morphological model of a P-wave in the A-EGM; and upon the occurrence of each P/R-Trigger signal, providing a morphological analysis of the error signal to a morphological model of the P-wave in the A-EGM only during a morphology time window, wherein only P-waves in the error signal are found to match the P-wave morphological model and are distinguished from residual noise signals in the error signal.

7. The method of claim 6, further comprising the step of synchronizing the timing of generation of the R-trigger signal to a corresponding P/R-Trigger signal.

8. The method of claim 6, further comprising the steps of:

providing a P-Marker signal when the morphological analysis shows a high correlation of the error signal with the P-wave morphological model; and providing an R-Marker signal when the morphological analysis shows a low correlation of the error signal with the P-wave morphological model.

9. The method of claim 6, wherein the medical device is a dual chamber cardiac pacemaker of the type operating in an atrial synchronous pacing mode and having at least an atrial sense amplifier coupled with an atrial sense electrode for placement in relation with an atrium for detecting the A-EGM, a ventricular sense amplifier coupled with a ventricular pace/sense electrode for placement in relation with a ventricle for detecting the ventricular electrogram (V-EGM), an atrial-ventricular (A-V) delay interval timer, and a ventricular pace (V-PACE) pulse generator for applying V-PACE pulses to said ventricular pace/sense electrode, the method further comprising the steps of:

sensing said A-EGM from said atrial sense electrode;

sensing said V-EGM from said ventricular pace/sense electrode;

generating an atrial sense P-Marker signal when the morphological analysis shows a high correlation of the error signal with the P-wave morphological model; and commencing the A-V delay interval in response to the P-Marker signal.

10. The method of claim 9, further comprising the step of providing an R-Marker signal when the morphological analysis shows a low correlation of the error signal with the P-wave morphological model.

11. The method of claim 10, wherein said cardiac pacemaker is operable in multiple operating modes influenced by the sequence of P-Marker signals and R-Marker signals.

12. The method of claim 10, wherein said cardiac pacemaker is operable in an anti-tachyarrhythmia pacing mode in response to a sequence of high rate P-Marker signals.

13. In a medical device having multiple operating modes, a method of ensuring that atrial sense events result from intrinsic P-waves originating in the atria and are not far field R-waves for determining the operating mode of the medical device, the medical device having at least an atrial sense amplifier coupled with an atrial sense electrode for placement in relation with an atrium for detecting the atrial electrogram (A-EGM), and a ventricular sense amplifier coupled with a ventricular pace/sense electrode for placement in relation with a ventricle for detecting the ventricular electrogram (V-EGM), the method comprising the steps of:

sensing the A-EGM from said atrial sense electrode, the A-EGM including the P-waves and far field R-waves;

sensing the V-EGM from said ventricular sense electrode, the V-EGM including the R-waves;

generating atrial channel trigger (P/R-Trigger) signals in response to P-waves and far field R-waves in the A-EGM;

generating ventricular trigger (R-Trigger) signals in response to R-waves in the V-EGM;

synchronizing the timing of generation of the R-trigger signal to a corresponding P/R-Trigger signal;

adaptively filtering the A-EGM signal by applying the R-Trigger signal to the input of an adaptive filter and combining the A-EGM signal with the output signal of the adaptive filter to which combined error signal is applied as a feedback signal to derive the error signal representing the A-EGM signal in which the far field R-wave is adaptively canceled;

providing a morphological model of a P-wave in the A-EGM;

upon the occurrence of each P/R-Trigger signal, template matching the error signal to the morphological model of the P-wave in the A-EGM only during a morphology time window;

generating an atrial sense marker when a P-wave in the error signal matches the morphological model; and setting the operating mode of the medical device in response to the atrial sense marker.

14. In a medical device having an operating mode responsive to the detection of an atrial tachyarrhythmia, a method of ensuring that atrial sense events result from intrinsic P-waves originating in the atria and are not far field R-waves for determining the operating mode of the medical device, the medical device having at least an atrial sense amplifier coupled with an atrial sense electrode for placement in relation with an atrium for detecting the atrial electrogram (A-EGM), and a ventricular sense amplifier coupled with a ventricular pace/sense electrode for placement in relation with a ventricle for detecting the ventricular electrogram (V-EGM), the method comprising the steps of:

sensing the A-EGM from said atrial sense electrode, the A-EGM including P-waves and far field R-waves;

sensing the V-EGM from said ventricular sense electrode, the V-EGM including R-waves;

generating atrial channel trigger (P/R-Trigger) signals in response to P-waves and far field R-waves in the A-EGM;

generating ventricular trigger (R-Trigger) signals in response to R-waves in the V-EGM;

synchronizing the timing of generation of the R-trigger signal to the P/R-Trigger signal;

adaptively filtering the A-EGM signal by summing the A-EGM signal with the output signal of an adaptive filter to which the R-Trigger signal is applied as the input signal to derive an error signal representing the A-EGM signal in which the far field R-wave is adaptively canceled;

providing a morphological model of a P-wave in the A-EGM;

upon the occurrence of each P/R-Trigger signal, template matching the error signal to the morphological model of the P-wave in the A-EGM only during a morphology time window;

generating an atrial marker signal when a P-wave in the error signal matches the morphological model; and determining the existence of an atrial tachyarrhythmia from the atrial marker signals.

15. Apparatus for processing a sensed atrial electrogram in conjunction with a sensed ventricular electrogram to accurately distinguish atrial P-waves from far field ventricular events, including far field R-waves and to avoid oversensing such far field ventricular events as atrial sense events and undersensing atrial events occurring within a fusion beat masked by a far field ventricular event in the atrial electrogram, comprising:

means for generating atrial channel trigger signals in response to sensed P-waves and far field R-waves in the atrial electrogram;

means for generating ventricular trigger signals in response to sensed R-waves in the ventricular electrogram;

means operable in response to each ventricular channel trigger signal for adaptively filtering the sensed atrial electrogram signal for an adaptive filter time window only to remove the far field R-wave signal from the sensed atrial electrogram signal while avoiding adaptive filtering of the sensed atrial electrogram signal at other times; and means operable in response to each atrial channel trigger signal for subjecting the adaptively filtered, sensed atrial electrogram signal to a morphological analysis with respect to a morphological model of a P-wave only during a morphology time window, wherein P-waves in the sensed atrial electrogram signal are detected and far field R-waves in the sensed atrial electrogram signal are not mistakenly detected as P-waves, while avoiding morphological analysis of the sensed atrial electrogram at other times.

16. The apparatus of claim 15, wherein the step of generating atrial trigger signals further comprises:

means for establishing at least one atrial sense criterion;

means for comparing the sensed atrial electrogram signal to the atrial sense criterion and deriving an atrial channel trigger signal each time a sensed atrial electrogram signal characteristic satisfies the atrial sense criterion.

17. The apparatus of claim 15, wherein the step of generating ventricular trigger signals further comprises:

means for establishing at least one ventricular sense criterion;

means for comparing the sensed ventricular electrogram signal to the ventricular sense criterion and deriving a

21 ventricular channel trigger signal each time a sensed ventricular electrogram signal characteristic satisfies the ventricular sense criterion.

18. The apparatus of claim 15, further comprising:

means for synchronizing the timing of generation of the ventricular trigger signal to a corresponding atrial trigger signal.

19. The apparatus of claim 15, incorporated into a system of the type having at least an atrial sense amplifier coupled with an atrial sense electrode for placement in relation with an atrium for detecting the atrial electrogram and a ventricular sense amplifier coupled with a ventricular sense electrode for placement in relation with a ventricle for detecting the ventricular electrogram, a method of discriminating atrial P-waves from far-field ventricular R-waves, both appearing in the atrial electrogram, further comprising:

means for sensing the atrial electrogram from said atrial sense electrode, the sensed atrial electrogram signal including the P-waves and far-field R-waves; and means for sensing the ventricular electrogram from said ventricular sense electrode, the sensed ventricular electrogram signal including R-waves.

20. In a dual chamber cardiac medical device, apparatus for discriminating atrial P-waves from far-field ventricular R-waves, both appearing in the A-EGM, and to avoid oversensing such far field R-waves as P-waves and undersensing P-waves occurring within a fusion beat masked by a far field R-wave, comprising:

means for detecting the atrial electrogram (A-EGM);

means for detecting the ventricular electrogram (V-EGM);

means for generating atrial channel trigger (P/R-Trigger) signals in response to P-waves and far field R-waves in the A-EGM;

means for generating ventricular trigger (R-Trigger) signals in response to R-waves in the V-EGM;

means operable upon the occurrence of each R-Trigger signal for adaptively filtering the A-EGM signal by applying the R-Trigger signal to the input of an adaptive filter and combining the A-EGM signal with the output signal of the adaptive filter to which a combined error signal is applied as a feedback signal to derive the error signal representing the A-EGM signal in which the far field R-wave is adaptively canceled only during an adaptive filter time window;

means for providing a morphological model of a P-wave in the A-EGM; and means operable upon the occurrence of each P/R-Trigger signal for providing a morphological analysis of the error signal to a morphological model of the P-wave in the A-EGM only during a morphology time window, wherein only P-waves in the error signal are found to match the P-wave morphological model and are distinguished from residual noise signals in the error signal.

21. The apparatus of claim 20, further comprising means for synchronizing the timing of generation of the R-trigger signal to a corresponding P/R-Trigger signal.

22. The apparatus of claim 20, further comprising:

means for providing a P-Marker signal when the morphological analysis shows a high correlation of the error signal with the P-wave morphological model; and means for providing an R-Marker signal when the morphological analysis shows a low correlation of the error signal with the P-wave morphological model.

22

23. The apparatus of claim 20, wherein the medical device is a dual chamber cardiac pacemaker of the type operating in an atrial synchronous pacing mode and having at least an atrial sense amplifier coupled with an atrial sense electrode for placement in relation with an atrium for detecting the A-EGM, a ventricular sense amplifier coupled with a ventricular pace/sense electrode for placement in relation with a ventricle for detecting the ventricular electrogram (V-EGM), an atrial-ventricular (A-V) delay interval timer, and a ventricular pace (V-PACE) pulse generator for applying V-PACE pulses to said ventricular pace/sense electrode, the apparatus further comprising:

means for sensing said A-EGM from said atrial sense electrode;

means for sensing said V-EGM from said ventricular pace/sense electrode;

means for generating an atrial sense P-Marker signal when the morphological analysis shows a high correlation of the error signal with the P-wave morphological model; and means for commencing the A-V delay interval in response to the P-Marker signal.

24. The apparatus of claim 23, further comprising means for providing an R-Marker signal when the morphological analysis shows a low correlation of the error signal with the P-wave morphological model.

25. The apparatus of claim 24, wherein said cardiac pacemaker is operable in multiple operating modes influenced by the sequence of P-Marker signals and R-Marker signals.

26. The apparatus of claim 24, wherein said cardiac pacemaker is operable in an anti-tachyarrhythmia pacing mode in response to a sequence of high rate P-Marker signals.

27. In a medical device having multiple operating modes, apparatus for ensuring that atrial sense events result from intrinsic P-waves originating in the atria and are not far field R-waves for determining the operating mode of the medical device, the medical device having at least an atrial sense amplifier coupled with an atrial sense electrode for placement in relation with an atrium for detecting the atrial electrogram (A-EGM), and a ventricular sense amplifier coupled with a ventricular pace/sense electrode for placement in relation with a ventricle for detecting the ventricular electrogram (V-EGM), the apparatus comprising:

means for sensing the A-EGM from said atrial sense electrode, the A-EGM including the P-waves and far field R-waves;

means for sensing the V-EGM from said ventricular sense electrode, the V-EGM including the R-waves;

means for generating atrial channel trigger (P/R-Trigger) signals in response to P-waves and far field R-waves in the A-EGM;

means for generating ventricular trigger (R-Trigger) signals in response to R-waves in the V-EGM;

means for synchronizing the timing of generation of the R-trigger signal to a corresponding P/R-Trigger signal;

means for adaptively filtering the A-EGM signal by applying the R-Trigger signal to the input of an adaptive filter and combining the A-EGM signal with the output signal of the adaptive filter to which combined error signal is applied as a feedback signal to derive the error signal representing the A-EGM signal in which the far field R-wave is adaptively canceled;

means for providing a morphological model of a P-wave in the A-EGM;

means operable upon the occurrence of each P/R-Trigger signal for template matching the error signal to the morphological model of the P-wave in the A-EGM only during a morphology time window;

means for generating an atrial sense marker when a P-wave in the error signal matches the morphological model; and means for setting the operating mode of the medical device in response to the atrial sense marker.

28. In a medical device having an operating mode responsive to the detection of an atrial tachyarrhythmia, apparatus for ensuring that atrial sense events result from intrinsic P-waves originating in the atria and are not far field R-waves for determining the operating mode of the medical device, the medical device having at least an atrial sense amplifier coupled with an atrial sense electrode for placement in relation with an atrium for detecting the atrial electrogram (A-EGM), and a ventricular sense amplifier coupled with a ventricular pace/sense electrode for placement in relation with a ventricle for detecting the ventricular electrogram (V-EGM), said apparatus comprising:

means for sensing the A-EGM from said atrial sense electrode, the A-EGM including P-waves and far field R-waves;

means for sensing the V-EGM from said ventricular sense electrode, the V-EGM including R-waves;

means for generating atrial channel trigger (P/R-Trigger) signals in response to P-waves and far field R-waves in the A-EGM;

means for generating ventricular trigger (R-Trigger) signals in response to R-waves in the V-EGM;

means for synchronizing the timing of generation of the R-trigger signal to the P/R-Trigger signal;

means for adaptively filtering the A-EGM signal by summing the A-EGM signal with the output signal of an adaptive filter to which the R-Trigger signal is applied as the input signal to derive an error signal representing the A-EGM signal in which the far field R-wave is adaptively canceled;

means for providing a morphological model of a P-wave in the A-EGM;

means operable upon the occurrence of each P/R-Trigger signal for template matching the error signal to the morphological model of the P-wave in the A-EGM only during a morphology time window;

means for generating an atrial marker signal when a P-wave in the error signal matches the morphological model; and means for determining the existence of an atrial tachyarrhythmia from the atrial marker signals.

* * * * *